United States Patent [19]

Hashizume et al.

[11] Patent Number: 5,221,521

[45] Date of Patent: Jun. 22, 1993

[54] SAMPLE LIQUID DILUTION SYSTEM FOR ANALYTICAL MEASUREMENTS

[75] Inventors: Yoshio Hashizume, Akashi; Akio Kariyone, Kyoto; Ryuzo Hayashi, Higashiosaka, all of Japan

[73] Assignee: Kanzaki Paper Mfg. Co., Ltd., Tokyo, Japan

[21] Appl. No.: 735,911

[22] Filed: Jul. 25, 1991

[30] Foreign Application Priority Data

Jul. 26, 1990 [JP] Japan .................. 2-200400
Jul. 30, 1990 [JP] Japan .................. 2-202877

[51] Int. Cl.$^5$ .................. B01L 11/00; G01N 1/00
[52] U.S. Cl. .................. 422/100; 422/103; 422/81; 436/179; 436/180; 436/174; 436/52; 436/53
[58] Field of Search .................. 422/100, 101, 103, 81, 422/82, 110; 436/179, 174, 180, 52, 53; 73/863.02, 863.03, 863.61

[56] References Cited

U.S. PATENT DOCUMENTS

| | | | |
|---|---|---|---|
| 4,263,406 | 4/1981 | Bostick et al. | 435/291 |
| 4,315,754 | 2/1962 | Ruzicka et al. | 422/81 |
| 4,424,276 | 1/1984 | Clark et al. | 436/50 |
| 4,504,443 | 3/1985 | Hanson et al. | 422/81 |
| 4,960,711 | 10/1990 | Aoki et al. | 436/124 |
| 5,019,515 | 5/1991 | Gisin et al. | 422/81 |
| 5,080,866 | 1/1992 | Petty et al. | 422/80 |

FOREIGN PATENT DOCUMENTS 0311588 4/1989 European Pat. Off. .
3908040A1 9/1990 Fed. Rep. of Germany .

OTHER PUBLICATIONS

J. Ruzicka et al., Analytica Chimica Acta, 114 (1980) pp. 19-44.
Clark et al., Analytical Chemistry, vol. 61, No. 15, pp. 1773-1778 (1989).

*Primary Examiner*—James C. Housel
*Assistant Examiner*—Long V. Le
*Attorney, Agent, or Firm*—Wenderoth, Lind & Ponack

[57] ABSTRACT

A liquid dilution system which dilutes a sample to be analyzed with a carrier to supply a diluted sample-containing liquid to an analytical measurement apparatus of flow type. The inventive dilution system features simplicity and versatility as compared to conventional automatic apparatus with robot concept, and the present system comprises: a first carrier pump for feeding a first carrier; a sample injection unit for injecting the sample into the first carrier; a main passage for flowing a liquid from the sample injection unit to a detector unit of an analytical measurement apparatus; a branching device located downstream of the sample injection unit for forming a branched passage to remove a liquid mass partially from the main passage; a confluence unit located downstream of the branching unit for confluencing a second carrier; and a second carrier pump for feeding the second carrier to the confluence unit. Dilution and mixing of the sample with a carrier is done twice, once at the sample injection and then again at confluence.

6 Claims, 8 Drawing Sheets

SAMPLE LIQUID DILUTION SYSTEM FOR ANALYTICAL MEASUREMENTS

FIELD OF THE INVENTION

This invention relates to a system or apparatus for diluting a sample liquid to be analyzed and for feeding the same to a measurement apparatus for flow injection analysis. Substantially, this invention relates to a preparatory sector or pretreatment art which advantageously enables the flow injection analysis. The outline of the flow injection analysis will be known by the article: FLOW INJECTION ANALYSIS. PRINCIPLES, APPLICATIONS AND TRENDS (Analytica Chimica Acta 114 (1980) 19–44).

DESCRIPTION OF THE RELATED ART

Conventionally, operations related to carry out measurements with use of analytical apparatus, such as a spectrophotometer, atomic absorption photometer, and other various analytical apparatus to produce electrochemical output, have been convenienced by employing the flow injection type measurement, wherein a sample liquid to be analyzed is fed in a flowing or moving state into a flow cell which is arranged in a measurement apparatus and, while the sample liquid passes through the flow cell, various observation means are applied to the flowing sample liquid to perform the intended measurements.

Then, in order to prepare for the flow injection type measurement, a sample to be analyzed should be dissolved or incorporated or injected into a carrier liquid so that a homogeneous sample liquid will be obtained.

The flow injection type analysis features the merit of eliminating personal differences attendant with various operations, because manual discrete or batchwise operations including mixing, separating, causing a chemical reaction are avoided, or in other words, what would be done manually by humans is converted to operations taking place along a continuous flow.

However, in the flow injection analysis, a sample to be analyzed should be prepared to meet with working requirements, i.e. dynamic range, of the analytical apparatus. Difficulty found in most cases of this type is preparation of a sample solution having the sample diluted with a carrier liquid in a range of suitable concentration.

In the case where the dilution is carried out by humans, necessary operations include a taking-out of the sample and the carrier liquid each in a necessary amount and mixing both to obtain a diluted liquid. Such operations take time and tend to make errors due to experimental implements and personal qualities.

On the other hand, there has been known another approach to solve such problems. That is development of a machine with robot concept which will carry out the operations simulated to operations by humans.

However, this kind of automatic diluting machine generally has a narrow latitude as to the operable range for handling things, especially liquids. In the aspect of human simulated operations, such a machine is not versatile to carry out the job of dilution which requires repeated stirrings. As a result, such a mechanical operation takes longer time, and the machine parts which have contacted the liquids or charged matters during the operation should be washed well manually with difficulty due to complex structure. Such burdensome extra work and expensive cost or investment for the automatic machines have not been acceptable in most cases of analytical measurements.

SUMMARY OF THE INVENTION

In contrast to a human simulated automatic machine as noted above, the present invention intends to offer a new system or apparatus which is provided with application of conventional devices or gadgets, and/or supplies available normally in the field of analysis by arranging them in the form of a flow line in a unique manner. Therefore, a system of the present invention features dilution of the flow type and enables fast, accurate performance with simple construction or arrangement and less operation cost.

Essentially states, the present invention comprises the following features as a primary aspect, that is, a dilution system which comprises: a first pump to feed a first carrier to the system; a sample injection or input unit located downstream of the first pump to incorporate a sample to be measured into the flow of the first carrier; a main passage from the sample injection unit to a detector unit of an analytical measurement apparatus; a branching unit located downstream of the sample injection unit and upstream of a confluence unit (as will be apparent below) to branch off a portion of the flow mass in the main passage; a confluence unit for introducing a second carrier into the main passage, to which unit another pump is disposed to feed the second carrier into the main passage at a location downstream of the branching unit.

Other aspects and various advantages of the present invention will become apparent through the following description of embodiments with reference to the drawings.

BRIEF DESCRIPTION OF THE DRAWINGS

Therefore, FIGS. 1 to 6 are concerned with the same embodiments of the invention excepting the kind of detector unit.

Therefore, FIGS. 7 to 9 are concerned with the same embodiments of the invention excepting the kind of detector unit.

DESCRIPTION OF THE PREFERRED EMBODIMENTS

Figure 1:
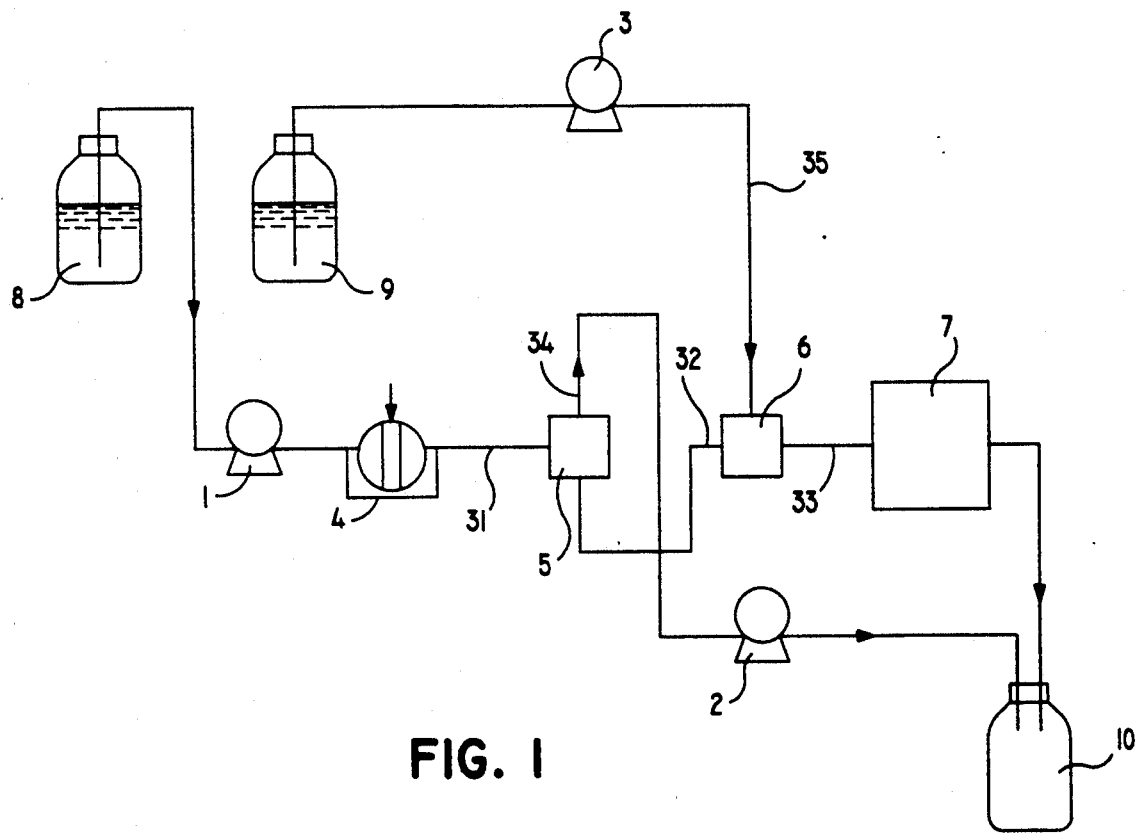
FIG. 1 shows a schematic diagram of one embodiment of the dilution system of the present invention, featuring use of three (3) pumps.
Figure 7:
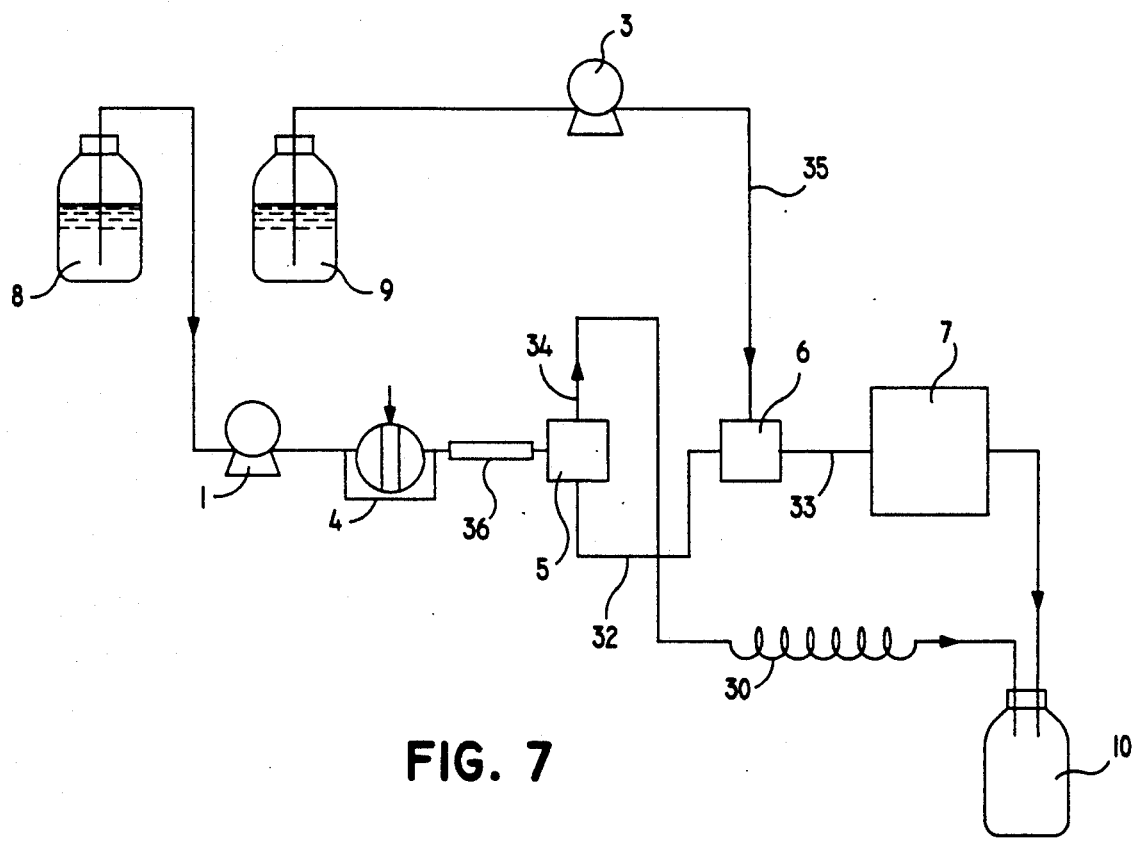
FIG. 7 shows a schematic diagram of another embodiment of the dilution system of the present invention, featuring use of two (2) pumps.

Referring to FIGS. 1 and 7, a first carrier, normally water or another solvent for a sample to be analyzed and stored in a vessel 8, is continuously fed by a first pump 1 to a sample injection unit 4, automatic sampler or manual injector and the sample injected at the unit 4 is carried down to a detector unit 7 wherein some intended analytical measurement is conducted thereon. The term "main passage" in the embodiments means a tubular route or flow line 31, 32, and 33 from the sample injection unit 4 to the detector unit 7.

On the way of the main passage, a branching unit 5 and a confluence unit 6 are fitted, the branching unit 5 being located downstream of the sample injection unit 4 and the confluence unit 6 being downstream of the branching unit 5.

The sample injected at the unit 4 is carried by the first carrier to the branching unit 5, wherein a portion of the flow mass is continuously removed away to take another route of branching route 34 toward the pump 2 in FIG. 1 or a pressure adjuster 30 in FIG. 7. That is, some amount of the sample to be analyzed is necessarily decreased at the branching unit 5 and in turn, the decreased mass of the liquid is fed downstream. Now, if branching route 34 is on the upside, small buffers included in the liquid can be eliminated. Consequently possible trouble to be caused with bubbles which sometimes appear can be avoided.

At the confluence unit 6, a second carrier stored in a vessel 9 is charged into the flow or main passage with aid of the pump 3, thereby a dilution continuously takes place with a certain rate or time. The second carrier causes the dilution as well as an increase of the flow mass which was once decreased at the branching unit 5.

The increase of the flow mass will act as some adjustment or control of a flow rate in passing through the detector unit 7. That is, it will help to keep a measuring time span allowable for producing waves, i.e. output which may appear on an observation screen, etc, and may help to keep the liquid mass flowing or moving at a rather high flow rate during the measurement.

One available means for removing or branching off some amount of the liquid with a constant ratio is to set a device for adjusting a resistance to leak. As shown in FIG. 7, a pressure adjuster 30 is fitted on the path of the branched passage. Then, this means is meant for causing spontaneous branching or leak. Therefore, another way is to set a suction pump 2 (see FIG. 1) on the same route, and is meant for applying mechanical suction force.

The pressure adjuster 30 mentioned above is permitted to be a valve. In addition, thin tubes which are ordinarily used in the flow injection analysis will be conveniently reasonable length and if necessary coiled. For example, a stainless tube or fluorocarbon resin (for example, polytetrafluoroethylene) pipe having an inner diameter of 0.25 to 2.0 mm is applied in a wound form to gain a certain length as will be viewed by 30 in FIG. 7. This extra extension of the tubular passage is advantageous to attain the purpose with simple, easy preparation and to effect different pressure resistances with stability, and ready changing a tube length necessary thereto is allowable. These tubes are ordinarily adjusted to a length of 2 to 30 m.

In this case, the pressure resistance is inversely proportional to the square power of an inner diameter of a tube, which suggests that use of a thinner or smaller diameter tube achieves the purpose with a relatively short tube in length. But care should be taken on the point that the smaller tube is likely to suffer more often a plugging or abnormal surging of the resistance which is caused by foreign solid matters if contained in the liquid. Accordingly, recommended size is preferably 0.5 to 2.0 mm inner diameter.

Based on the arrangement taken in the present invention, a throughput dilution ratio or time may be determined by choosing a ratio of branching off and a ratio of confluence. Referring to this point further, in the case of using the leak pressure resistance tube as a pressure adjuster in FIG. 7, adjustment to increase a dilution ratio is recommended to be effected by shortening a length of the passage to give less passage resistance and by increasing a share of the liquid flowing into the branched route. However, extreme shortening of the passage will produce other troubles, for example, inability of the sample to reach the detector unit or instability of the leak resistance pressure. In view of such factors, in the case of a tube of 0.5 mm inner diameter, preferable length is somewhat longer than 3 m, more preferably, somewhat longer than 5 mm.

Alternatively, in the case of setting the suction pump 2 to use a mechanical suction force, application of more suction will increase a dilution ratio or time. However, this suction volume should be less than the delivery volume of the first pump 1.

In addition, dilution is permitted to be changed by adjusting a delivery rate of the pump 3 for handling the second carrier. More delivery gives more dilution. Advantage with the case of FIG. 1 lies in easiness of setting up or calculating a target dilution ratio or time with use of data on deliveries of three pumps 1, 2, and 3.

The branching unit 5 and the confluence unit 6 are a type of pipe fitting that can connect three pipe lines, as shown in FIG. 2, so that the three pipe lines meet at a point inside the pipe fitting. In the simplest form of arrangement, two of the three pipe lines are arranged in a straight line with the remaining one meeting them at right angles, or the three pipe lines are arranged in the same plane in such a manner that they are spaced 120 degrees apart from each other. It will be appreciated that the connection arrangement of the pipe lines is not limited to the above examples and also that the pipe lines need not be disposed in the same plane as long as they are connected to each other at one point.

Also, as the material for the branching unit and the confluence unit, the same materials as usually used in pipes, such as stainless, polytetrafluoroethylene etc., can be used.

Figure 2A:
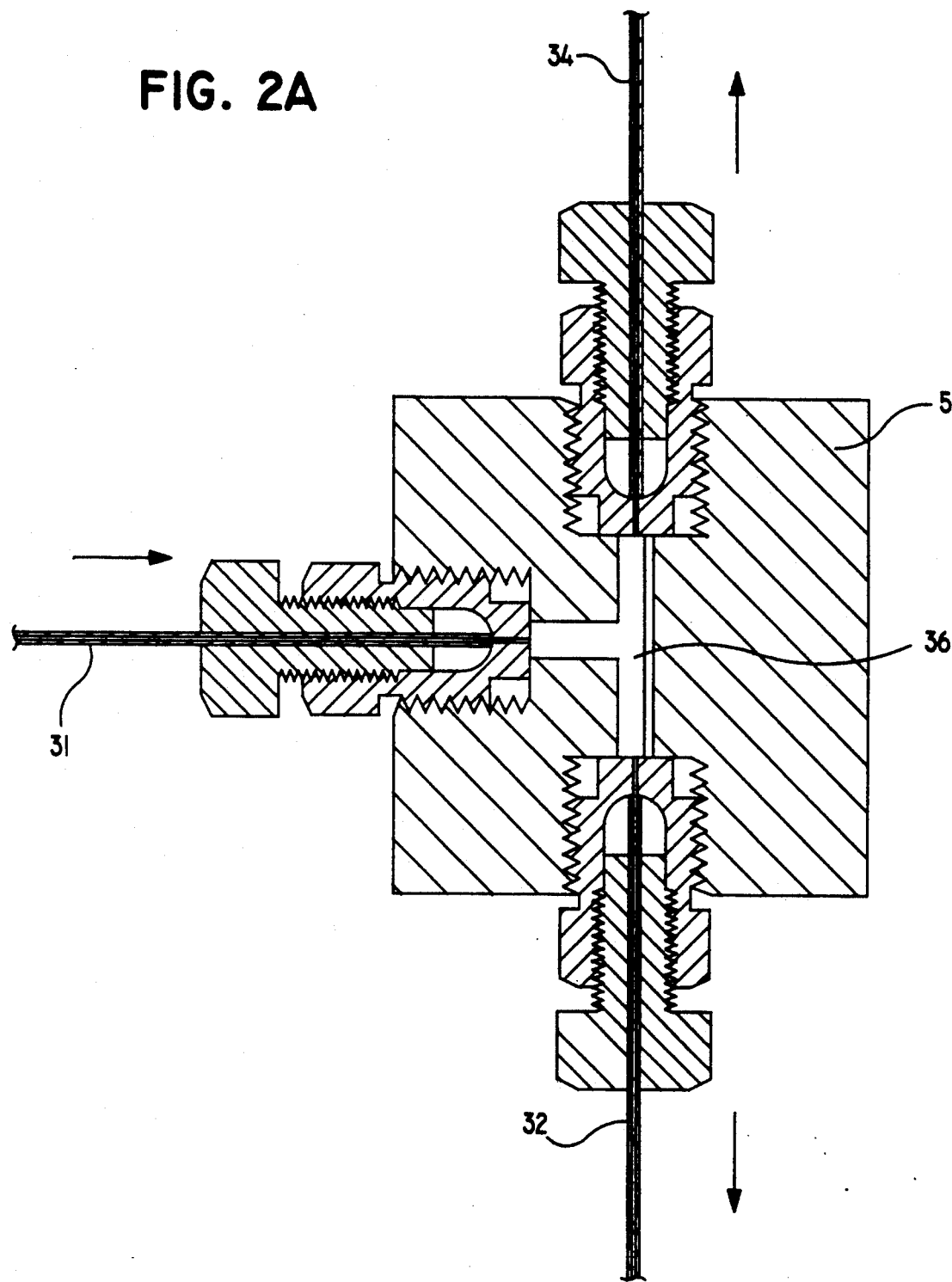
FIG. 2A shows a schematic drawing of a branching unit of the present invention.
Figure 2B:
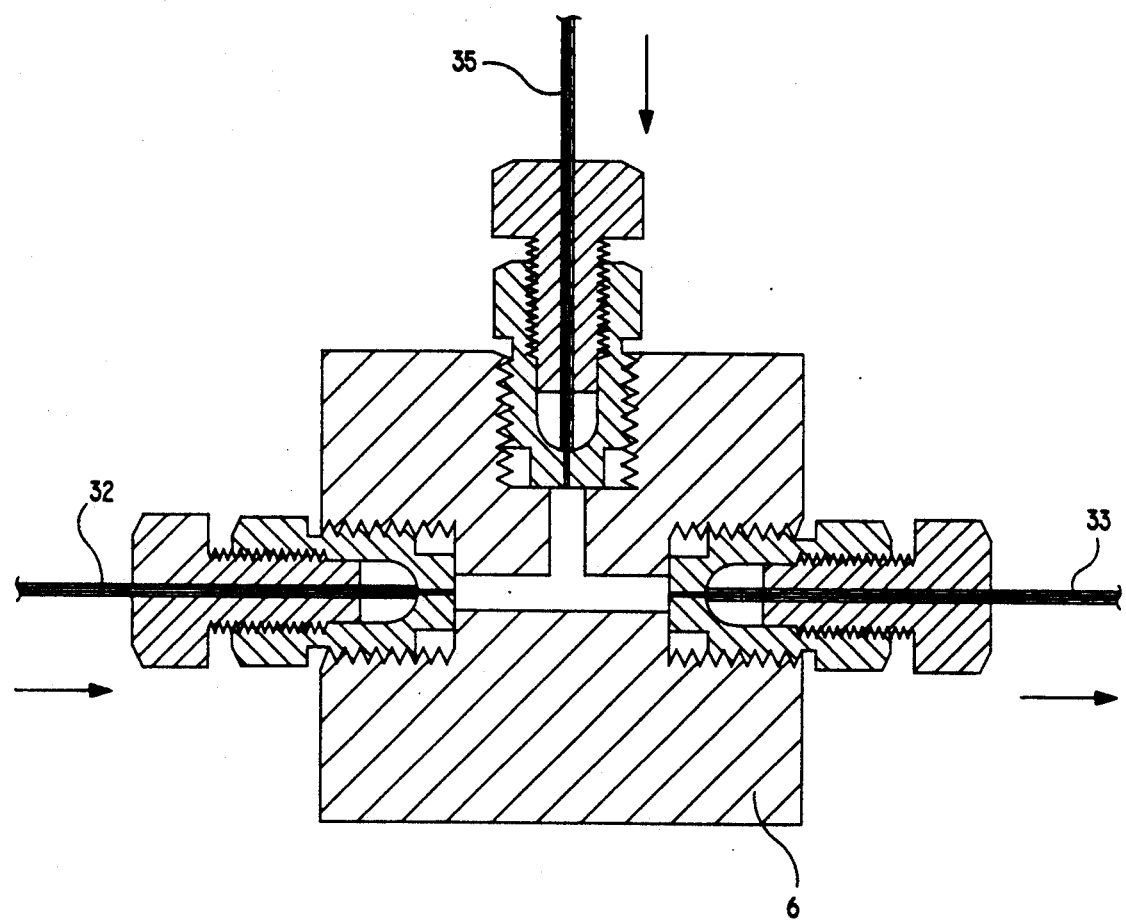
FIG. 2B shows a schematic drawing of a confluence unit of the present invention.

FIG. 2A shows an example of connection at the branching unit 5, in which the main flow passage 31 is connected to the left end, the main flow passage 32 to the lower end, and the branching flow passage 34 to the upper end. FIG. 2B shown as example of connection at the confluence unit 6, in which the main flow passage 32 is connected to the left end, the main flow passage 33 to the right end, and the confluence passage 35 to the upper end.

At the branching unit 5, it is recommended to set a port for branching off to be on the upside of the tube so that possible small bubbles included in the liquid will be eliminated or removed away from the main passage.

Examples of the quantity measuring pump 1 include a so-called quantitative discharge pump which sucks and discharges carrier in a short cycle using a plunger, a so-called syringe pump which sucks and discharges carrier in a long cycle using a syringe, a peristaltic pump which discharges carrier by pressing an elastic tube with a plurality of rollers, and others.

When the system is operated with first and second pumps 1, 3 of plunger delivery type, for example, it is possible that a flow in the branched passage becomes unstable due to pulsation of delivery actions by the pumps, but this trouble may be overcome by enlarging the actual inside volume of the branching chamber 36 to be more than the volume of one delivery action of either pump concerned.

According to the invention, it is desirable that the internal capacity of the branching unit 5, i.e. the capacity of the branch chamber 36, be not smaller than the single discharge capacity of either the first pump 1 or the second pump 3. The branch chamber 36 is a chamber having a space whose cross section is larger than the cross section of any of the three pipe lines connected to the branching unit taken perpendicular to the flow direction.

The invention has the advantage that when the capacity of the branch chamber 36 is regulated as described above, the volume corresponding to the single discharge capacity of the pump is allowed to stay in the branch chamber for a time at least equal to or longer than the single discharge time thereof, which serves to ease abrupt separation and thus provides stable branch flow.

On the other hand, if the space capacity of the branch chamber is smaller than the single discharge capacity of the pump, a variation in the flow division ratio may be caused depending on whether the pump is discharging the carrier or sucking the carrier at the time the sample solution is introduced into the branch chamber.

The pump provides less pulsation and is therefore more advantageous as its single discharge capacity is smaller. The discharge capacity is preferably 100 $\mu l$ or less, and more preferably 50 $\mu l$ or less, but in view of matching accuracy, it is desirable that the pump have a single discharge capacity of about 0.1 $\mu l$ at minimum.

Also, as the capacity of the branch chamber increases, the solution will stay longer therein, resulting in a longer analyzing time. Therefore, the capacity of the branch chamber should be equal to or larger than the single discharge capacity of the pump, preferably within the range of one to twenty times, and more preferably one to ten times, the single discharge capacity of the pump.

It has previously been believed that a flow divider used in an FIA analyzer should have an internal capacity as small as possible so as to increase the measuring speed.

As shown in FIG. 2(1), the pipe lines 31, 32, and 34 are connected to the branching unit 5 so that the sample fed through the pipe line 31 is split inside the branch chamber 36 and is delivered in opposite directions in the example shown here. Besides the arrangement shown in FIG. 2(1) in which the flow is diverted in two opposite directions each at right angles to the inflow pipe line, other arrangements may be employed, including an arrangement in which the flow is split into respective branch lines forming a branch angle of 120 degrees, etc.

Each of the pumps stated herein is not specifically limited in type as long as it actively generates a single liquid flow, and various known types of pump may be used for this purpose. As the pumps for use in the present invention, a so-called multiple head type pump may also be used which comprises a plurality of pumps connected in parallel with each other to generate a single liquid flow and to reduce pulsation. In this case also, the single discharge quantity of the pump is defined as the discharge capacity of each pump head.

In use of pumps, if each pump has some pulsation in delivery, parallel connection of more than one pump will lessen it, and it is preferable to use a composite pump structured of plural pumps so as to give one delivery flow with less pulsation.

The dilution system of the present invention will be connected to an analytical apparatus equipped with an external detector unit 7, such as spectrophotometer, atomic absorption photometer, apparatus to produce electrochemical output, and other various analytical apparatus.

Preferable carriers are organic solvents, buffer solutions, and reagent solutions. In the case where an external detector unit 7 includes a detector of electrochemical nature, such as an enzyme immobilized electrode, the first and second carriers are permitted to be the same buffer solution, and the vessels 8 and 9 may be consolidated into one vessel. Alternatively, the first carrier may be water, which will reduce the operation cost.

As for the sample handling at the injection unit 4, it is advisable to use a manual injector or automatic sampler, commercially available. In view of convenience and accuracy, preferably is the automatic sampler which is, for example, contrived to transfer plural samples arranged on a table in the order from the places disposed to a place for sampling, and to put a needle into the sample to extract a predetermined volume thereof bu sucking, and then to take the extract to a port for sample injection.

It is generally assumed that samples are in good condition to be injected as they are, but if some solid or floating matter is found in a liquid sample, pretreatment for elimination, such as by filtration is recommended to avoid possible trouble in subsequent handling.

For the purpose of operating the dilution system of the present invention in stable condition, it is required to run the pumps at stable, constant flow rates and to minimize the pulsation, for which requirement it is advisable to intentionally impress some pressure so as to remove any local pressure changes. Specifically, it is desirable to fit a special piping in the path of the flow passages, for example, at two points across the detector unit 7, the branching unit 5 or the confluence unit 6. Also desirable is to install a device for buffering the pulsation downstream of a pump.

Examples of the pulsation buffering device include a unit partially constructed with an elastic wall, a unit which accumulates air in a recessed portion in the chamber and acts by compressing and expanding the air, and others.

In the case where an alcohol as the sample to be analyzed and water as the carrier are to be used, mixing these two kinds of liquids becomes difficult as the alcohol concentration increases. In an operation like this, a mixer can be installed in the passage between the sample injection unit 4 and the branching unit 5, for example, a device for causing turbulence or a line mixer such as mixing tube 36 which contains particles packed inside a tubular body.

In FIG. 1 or FIG. 7, this device whose construction omits carrier vessel 9, second pump 3 and confluence unit 6, is able to dilute the sample. If the inventive system is operated only with the first carrier and the branching unit, dilution is attained to some extent, but in such a case, an attempt of increasing the dilution effect by increasing the leak or branching off amount causes the flow rate of the sample liquid through the detector unit to become extremely low, hence causing an unreasonably longer measurement time. Conversely, an attempt of keeping a high liquid rate through the detector unit makes it impossible to increase the dilution ratio. Then, in order to keep a reasonable flow rate through the detector unit and simultaneously to gain a large dilution, it is required to increase the flow rate, but this invites consumption a larger amount of the carrier liquid and difficulty in setting a flow rate with the pump concerned.

Figure 10:
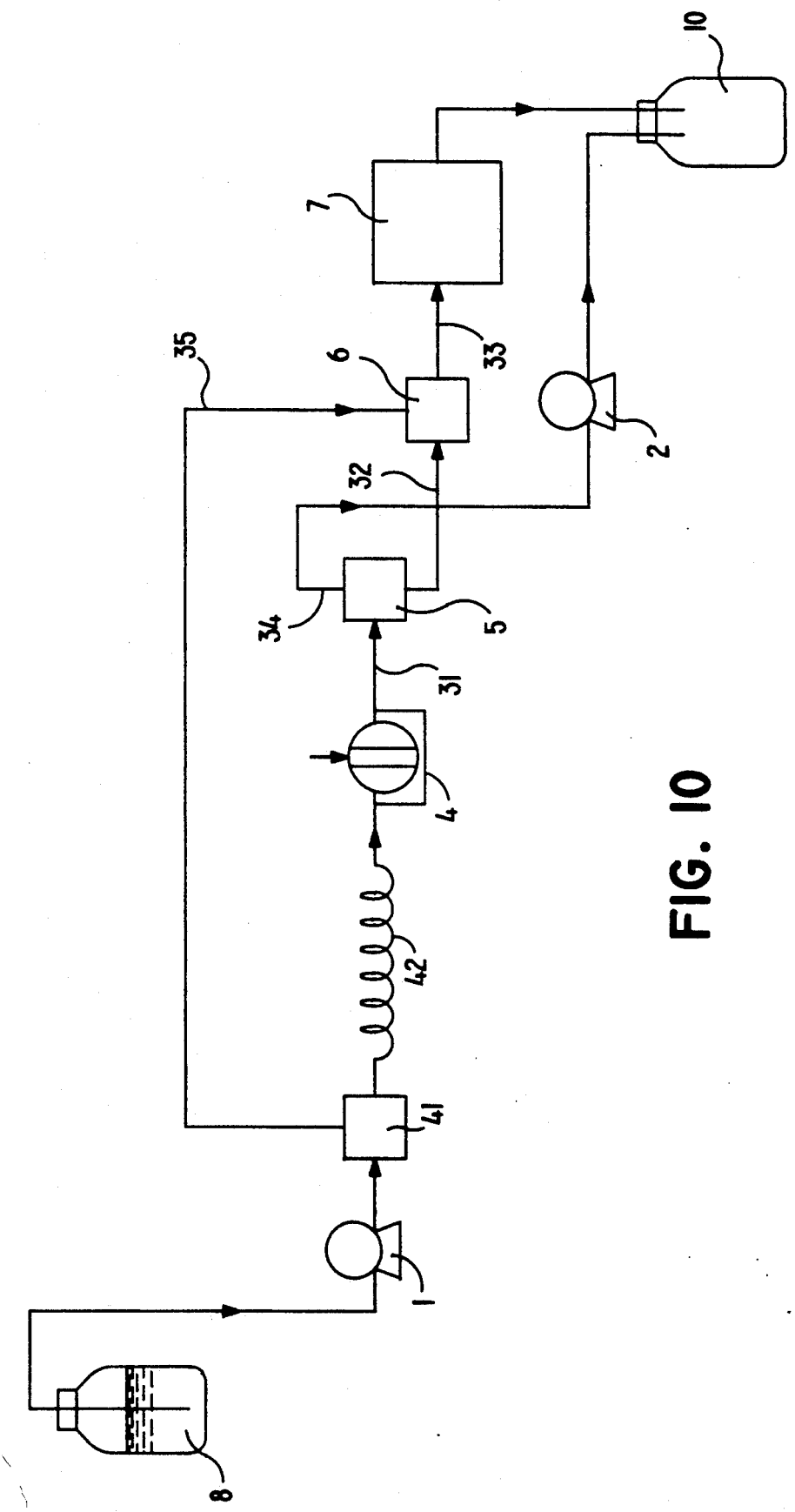
FIG. 10 shows a schematic diagram of another embodiment of the dilution system of the present invention.

Referring to FIG. 10, in use of one kind of carrier as both the first and the second ones, the pump 3 for the second carrier is saved. In this case, delivery of the pump 1 is divided into two passages by branching unit 41, one of which is directed to the confluence unit 6, and a flow share for the two routes will be controlled by fitting a pressure adjuster 42 being the flow passage at two points across the sample injection unit 4.

In the following, application examples of the present invention will be described, which are presented by way of illustration and therefore should not be construed as limiting the invention. Therein, the designation of only % unless otherwise specified is by weight.

EMBODIMENT 1

(1) Description of the Detector Unit

Figure 3:
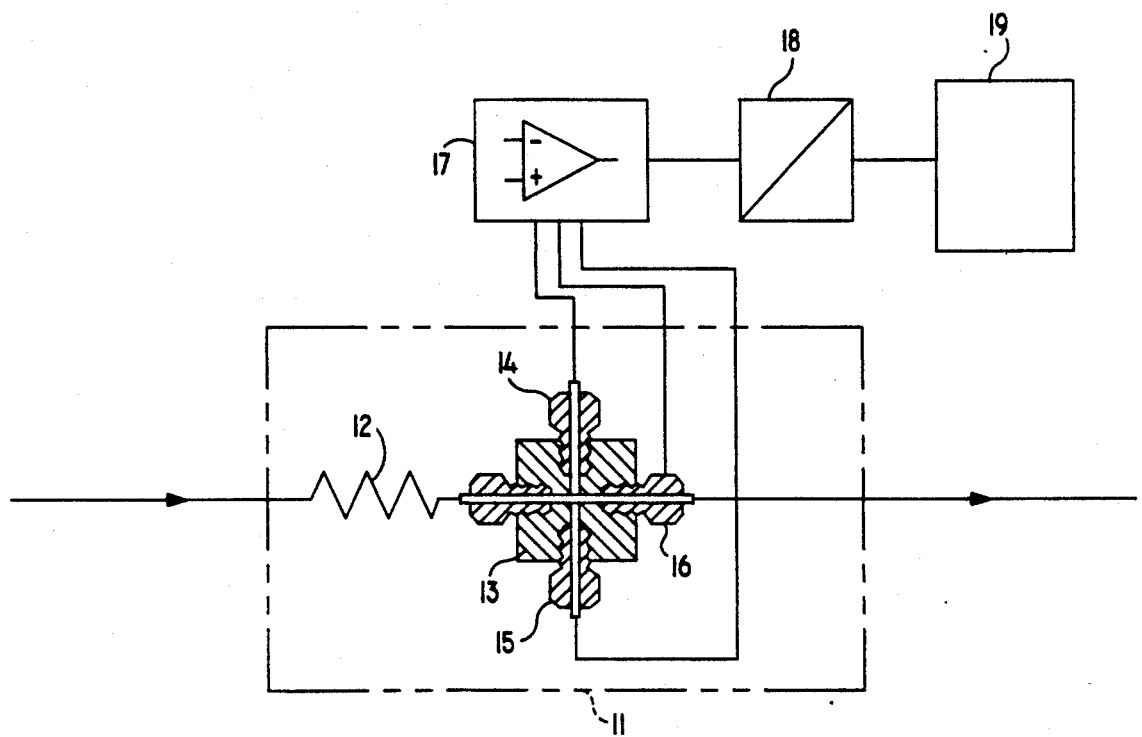
FIG. 3 shows a schematic drawing of a detector unit which is provided with a glucose sensing device and included in the arrangement of the present invention.

The detector unit 7 includes a glucose sensing device, of which schematic construction is shown in FIG. 3. Specifically, a flow cell 13 incorporating an immobilized enzyme electrode 14 which was prepared by immobilizing glucose oxidase on a platinum electrode, was disposed in a thermostat unit 11 so that glucose will be detected electrochemically by a potentiostat 17. Referring additionally to other devices, 12 is a coil mixer, 15 is an Ag/AgCl reference electrode, 16 is a counter electrode, an A/D converter 18, and 19 is a computer. Below details of the glucose detection unit will be given.

a. Immobilized Enzyme Electrode

A platinum wire having 2 mm diameter was wrapped sidewise with heat-shrinkable teflon (tradename), and one end of the wire was finished to be smooth with use of the file and the Emery paper of No. 1500 grade. This platinum wire was set as a working electrode, a platinum electrode of 1 cm square was set as a counter electrode, a saturated calomel electrode (will be noted SCE below) was set as a reference electrode, and these were subjected to electrolysis: in 0.1M sulfuric acid, +2.0 V or 5 min. and to sufficient washing with water, and then dried at 40° C. for 10 min. and in turn, immersed in dehydrated toluene containing 10% γ-aminopropyl-triethoxy-silane for 1 hr. followed by washing again. Immobilization of the enzyme onto the amino silane treated platinum wire was carried out in the following manner.

5 mg of glucose oxidase (prepared by Sigma Ltd. Type II) and 5 mg of bovine serum albumin (prepared by Sigma Ltd. Fraction V) were dissolved in 1 ml of 100 mM Na phosphate buffer solution (pH 7), in which gultaraldehyde was added to account for 0.2%. 5 μl of this mixed solution was quickly put on the platinum wire thus prepared to be cured at 40° C. for 15 min., and then the wire was stored in 100 mM of Na phosphate buffer solution (pH 6).

b. Method of Detection

The flow cell 13 was equipped with the immobilized enzyme electrode as described in the foregoing paragraph a as a working electrode, the Ag/AgCl reference electrode 15 as reference electrode to take opposite positions with the flow passage in between and to be perpendicular to the same passage, and with the counter electrode 16 made of stainless tube used as the same passage. The immobilized enzyme electrode 14 is given +0.6 V against the Ag/AgCl reference electrode 15 by the potentiostat 17. And all these devices were kept in the thermostat 11 in a range of 37° C.±0.2° C.

Current values detected by the potentiostat 17 were subjected to the current/voltage conversion to result in voltage values which would be, via an A/D converter 18 and hence as digital values, taken into computerized quantitative operations by the computer 19, wherein each detected intensity for each concentration was determined by a differential value which was found by subtracting a base from a wave peak.

(2) System for Measurements

Used was a measurement system, as shown in FIG. 1, including a flow type dilution apparatus or sample delivery system of the present invention (units referenced by 1, 2, 3, 4, 5, 6, 8, 9, and 10 were comprised) and the detector unit (referenced by 7). Each pump was of single plunger delivery type, of which delivery rate was set at: 1.0 ml/min. for the first pump 1, 0.9 ml/min. for the suction pump 2, 0.9 ml/min. for the second pump 3.

A first carrier and a second carrier were set to be the same. That is 100 mM of Na phosphate buffer solution (pH 6.0) containing 1 mM of sodium azide.

A sample injection unit 4 was an automatic sampler.

(3) Measurement Method and Results

After a temperature equilibrium was obtained at the thermostat 11, 5 μl of 300 mM glucose aqueous solution was input into the flow line, for which run output current values for a unit concentration were determined and found was 1.05 nA/mM. Therein the use of the present invention system proved that measurement on one sample having a high concentration requires one min.

COMPARATIVE EMBODIMENT 1

(1) The detector unit used was the same as in the foregoing embodiment 1.

(2) System for Measurements

From the layout of FIG. 1, the branched passage and the suction pump 2, confluence route and the second pump 3, branching unit 5, confluence unit 6 were removed. Hence the sample input unit 4 and the detector unit 7 were connected with a single tube. The system thus changed was used. Therein, the first pump 1 was set to have 1.0 ml/min rate.

(3) Measurement Method and Results

After a temperature equilibrium was obtained at the thermostat 11, 5 μl of 30 mM glucose aqueous solution was input into the flow line, for which run output current values for a unit concentration were determined and found was 10.92 nA/mM.

Evaluation of this comparative embodiment 1 against the foregoing embodiment 1 proved that the operation in the embodiment 1 diluted the input sample 10.4 times as compared to the comparative operation.

EMBODIMENT 2

(1) Description of the Detector Unit

Figure 4:
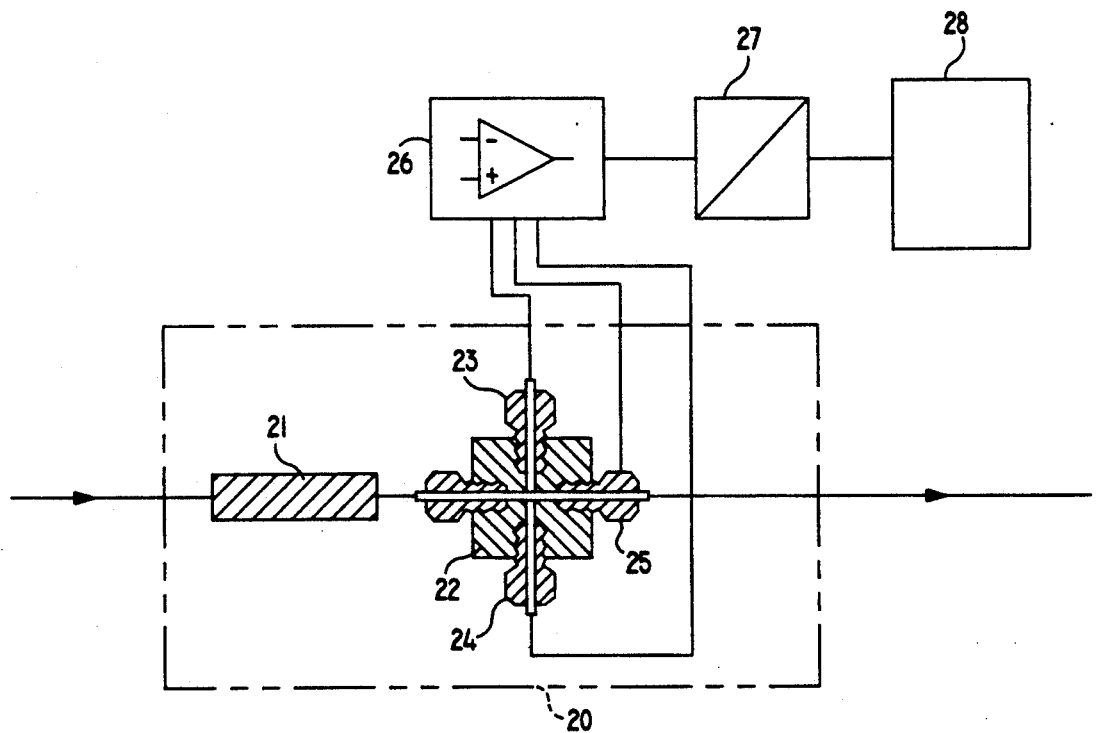
FIG. 4 shows another schematic drawing of a detector unit which is provided with an alcohol sensing device and included in the arrangement of the present invention.

The detector unit 7 includes an alcohol detector, of which schematic construction is shown in FIG. 4. Specifically, a flow cell 22 incorporating a hydrogen peroxide electrode 23, and an immobilized enzyme electrode 21 which was prepared by immobilizing alcohol oxidase, were disposed in a thermostat unit 20 so that alcohol will be detected electrochemically by a potentiostat 26. Below details of the alcohol detection unit will be given.

a. Hydrogen Peroxide Electrode

A platinum wire having 2 mm diameter was wrapped sidewise with heat-shrinkable teflon (tradename), and one end of the wire was finished to be smooth with use of the file and the Emery paper of No. 1500 grade. The platinum wire was set as a working electrode, a platinum electrode of 1 cm square was set as a counter electrode, a saturated calomel electrode (will be noted SCE below) was set as a reference electrode, and these were subjected to electrolysis: in 0.1M sulfuric acid, +2.0 V for 10 min. and to sufficient washing with water, and then dried at 40° C. for 10 min. and in turn, immersed in dehydrated toluene containing 10% γ-aminopropyl-triethoxy-silane for 1 hr. followed by washing again.

20 mg of bovine serum albumin (prepared by Sigma Ltd. Fraction V) was dissolved in 1 ml of distilled water, in which gultaraldehyde was added to account for 0.2%. 5 μl of this mixed solution was quickly put on the platinum wire thus prepared to be cured at 40° C. for 15 min., and then the wire was used as the hydrogen peroxide electrode.

b. Preparation of the Immobilized Enzyme Column 150 mg of fire brick (sieved 60 to 80 meshes) was dried well and immersed in 1 ml of dehydrated toluene containing 10% of γ-aminopropyl-triethoxy-silane for 1 hr., and then the silane coupling agent was washed with toluene and ethanol followed by drying at 120° C. for 2 hrs. After cooled, 0.5 ml of 5% gultaraldehyde aqueous solution was added and allowed to standing at room temperature for 1 hr. In turn, the carrier was washed well, wherein finally washed with Na phosphate buffer solution having pH 7 which was then eliminated as much as possible.

The amino silane carrier thus obtained was charged in the enzyme solution which contained 50 μl of alcohol oxidase (prepared by Sigma Ltd. enzyme solution derived from *Pichia pastolis*) diluted 10 times with Na phosphate buffer solution having pH 7.0, and then the charged solution was allowed to stand at ice temperature for 1 hr. and washed with the same buffer solution. The enzyme immobilized carrier thus prepared was filled or incorporated into the polytetra fluoroethylene tube having 3 mm outer diameter, 2 mm inner diameter, and 10 cm length, which was used as the alcohol oxidase immobilized column 21.

(2) System for Measurements

Used was a measurement system, as shown in FIG. 1, including a flow type dilution apparatus or sample delivery system of the present invention (units referenced by 1, 2, 3, 4, 5, 6, 8, 9, and 10 are comprised) and the detector unit (referenced by 7). Each pump is of single plunger delivery type, of which delivery rate was set at: 1.4 ml/min. for the first pump 1, 1.3 ml/min. for the suction pump 2, 0.9 ml/min. for the second pump 3.

A first carrier and a second carrier were set to be the same. That is, 100 mM of Na phosphate buffer solution (pH 7.0) containing 1 mM of sodium azide.

A sample injection unit 4 was an automatic sampler.

(3) Measurement Method and Results

Figure 5:
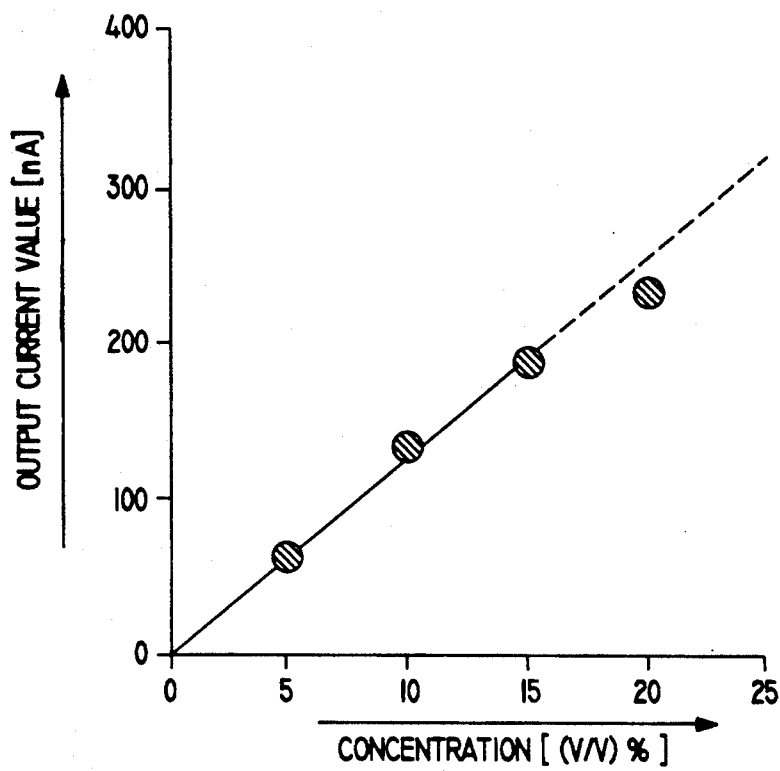
FIGS. 5 and 6 show graphs which were obtained by measurements with use of the alcohol sensing device as will be described in embodiments 2 and 3.

After a temperature equilibrium was obtained at the thermostat 20, 5 μl of ethyl alcohol aqueous solution having 5.0, 10.0, 15.0, 20.0 (v/v) % was input into the flow line, for which each run the output current values for each concentration were determined for 1 min. and the working line found was shown in FIG. 5.

Therein the output current value coefficient for a unit concentration was found to be 14.57 nA/(v/v) %. The working line indicates a linear relationship in the range of 5.0 to 15.0 (v/v) %, but at 20.0 (v/v) % concentration, the result is out of the linear relationship range.

COMPARATIVE EMBODIMENT 2

(1) The detector unit used was the same as in the foregoing embodiment 2.

(2) System for Measurements

From the layout of the embodiment, 2 the suction pump 2, the second pump 3, branching unit 5, confluence unit 6 were removed. Hence the sample input unit 4 and the detector unit 7 were connected with a single tube. The system thus changed was used. Therein, the first pump 1 was set to have 1.0 ml/min rate.

(3) Measurement Method and Results

The output current values measured by this alcohol detector unit have a limited range for giving the linear relationship, because hydrogen peroxide produced by the immobilized enzyme column depends on an oxygen concentration dissolved in the solution. The upper limit of the linear range with current outputs was tried to be found with use of a thin alcohol range of 0.1 to 2.0 (v/v) %. The result was approximate 380 nA and also found was that measurements are not permitted without use of the dilution system of the present invention in a range above about 1.8%.

Therein the output current value coefficient for a unit concentration was found to be 209.8 nA/(v/v) %.

Evaluation of this comparative embodiment 2 against the foregoing embodiment 2 proved that the operation in the embodiment 2 diluted the input sample 14.4 times as compared to the comparative operation.

EMBODIMENT 3

(1) The detector unit used was the same as in the foregoing embodiment 2.

(2) Systems for Measurements

Pulverized fire brick particles (60 to 80 mesh sieved) were packed into a polytetrafluoroethylene tube of 20 cm length and of outer, inner diameter; 3 mm, 2 mm. The packed tube, a mixing tube was set to span between the sample input unit 4 and the branching unit 5. Otherwise the same devices and units were used. Each pump was set to have the same rate as in the embodiment 2.

(3) Measurement Method and Results

Figure 6:
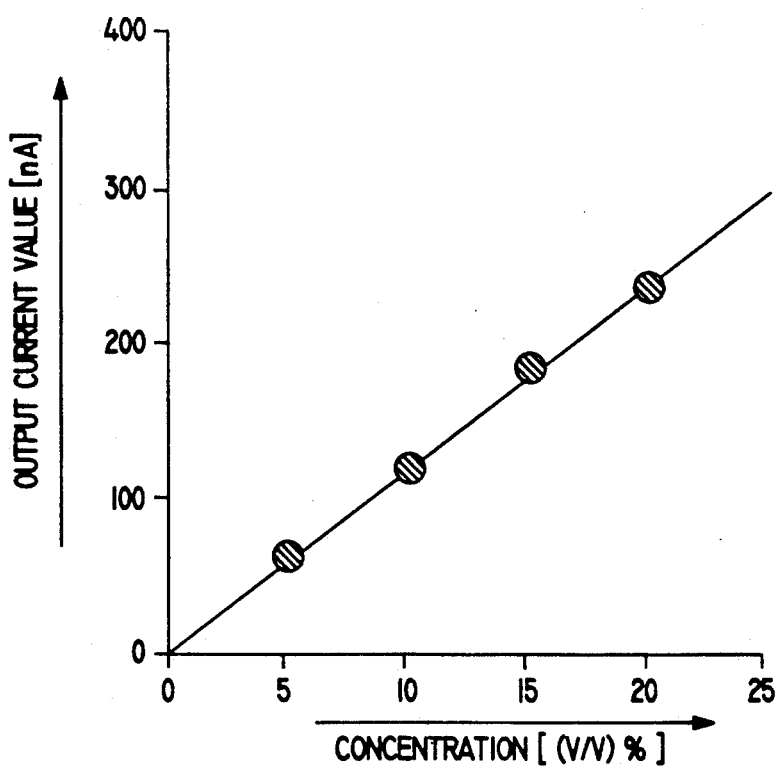

After a temperature equilibrium was obtained at the thermostat 20, 5 μl of ethyl alcohol aqueous solution each having 5.0, 10.0, 15.0, 20.0 (v/v) % was input into the flow line, for which run the output current values for each concentration werer determined for 1 min. and the working line found was shown in FIG. 6.

In this case, measured data were found to agree accurately with the linear working line until 20 (v/v) %, which was a higher concentration obtained in the embodiment 2. This superority is attributable to the improvement of mixing in this example as compared to the embodiment 2.

Therein, the current output value coefficient for a unit concentration was found to be 13.22 nA/(v/v) %. Note: the following embodiments employ the dilution system represented by FIG. 7 featuring inclusion of the leak pressure resistance 30.

EMBODIMENT 4

(1) Description of the Detector Unit

The detector unit 7 employed was the same as shown in FIG. 3 which was equipped with a glucose detector. Therefore, descriptions thereof are abbreviated.

a. Immobilized Enzyme Electrode

An immobilized enzyme electrode 14 used in the detector unit 7 was the same as described in the embodiment 1. Therefore, description thereof is abbreviated.

b. Method of Detection

Procedures applied in the detection were the same as described in the embodiment 1. Therefore, descriptions thereof are abbreviated.

(2) System for Measurements

Used was a measurement system, as shown in FIG. 7, including a flow type dilution apparatus or sample delivery system of the present invention (units referenced by 1, 2, 3, 4, 5, 6, 8, 9, and 10 were comprised) and the detector unit (referenced by 7).

A first carrier and a second carrier were set to be the same. That is, 100 mM Na phosphate buffer solution (pH 6.0) containing 1 mM sodium azide.

In layout of the dilution apparatus, the passage from the sample injection unit 4 to the branching unit 5 was formed with a stainless tube of 40 cm length and 0.5 mm inner diameter, passage from the branching unit 5 to the confluence unit 6 was formed with a stainless tube of 5 cm length and 0.5 mm inner diameter, passage from the confluence unit 6 to the flow cell included in the detector unit 7 was formed with a polytetrafluoroethylene tube of 125 cm length and 0.5 mm inner diameter. The sample injection unit 4 was an automatic sampler.

The pressure adjuster 30 to control a leak pressure resistance was formed with a polytetrafluoroethylene tube of 10 m length and 0.5 mm inner diameter so as to span from the branching unit 5 to the waste liquor bottle 10.

Each pump was of single plunger delivery type, of which delivery rate was set at: 0.8 ml/min. for the first pump 1, 1.0 ml/min. for the second pump 3, wherein actual leak rate was about 0.72 ml/min.

(3) Measurement Method and Results

After a temperature equilibrium was obtained at the thermostat 11, 5 μl of 300 mM glucose aqueous solution was input into the flow line, for which run current values for a unit concentration were determined and found was 0.79 nA/mM. Therein the sue of the present system proved that measurement on one sample having a high concentration requires only one min, so short time requirement.

COMPARATIVE EMBODIMENT 4

(1) The detector unit 7 used was the same as in the foregoing embodiment 4.

(2) System for Measurements

From the layout of FIG. 7, the second pump 3, branching unit 5, confluence unit 6 were removed and the sample injection unit 4 was connected directly to the detector unit 7 with a polytetrafluoroethylene tube of 170 cm length and of 0.5 mm inner diameter, and the first pump 1 was set at a rate 1.0 ml/min.

(3) Measurement Method and Results

After a temperature equilibrium was obtained at the thermostat 11, 5 μl of 30 mM glucose solution was input into the flow line, for which run output current values for a unit concentration were determined and found was 11.28 nA/mM.

Evaluation of this comparative embodiment 4 against the foregoing embodiment 4 proved that the operation in the embodiment diluted the input sample about 14.3 times as compared to the comparative operation.

EMBODIMENT 5

(1) Description of the Detector Unit

The detector unit 7 employed was the same as shown in FIG. 4 which was equipped with an alcohol sensing device. Therefore, descriptions thereof are abbreviated.

a. Hydrogen Peroxide Electrode

A hydrogen peroxide electrode 23 used in the detector unit 7 was the same as described in the embodiment 2. Therefore, description thereof is abbreviated.

b. Preparation of the Immobilized Column

Procedures applied in the preparation were the same as described in the embodiment 2. Therefore, descriptions thereof are abbreviated.

(2) System for Measurements

Used was a measurement system, as shown in FIG. 7, including a flow type dilution apparatus or sample delivery system of the present invention (units referenced by 1, 2, 3, 4, 5, 6, 8, 9, and 10 were comprised) and the detector unit (referenced by 7).

A first carrier and a second carrier were set to be the same. That is, 100 mM Na phosphate buffer solution (pH 7.0) containing 1 mM sodium azide.

In layout of the dilution apparatus, the passage from the sample injection unit 4 to the branching unit 5 was formed with a stainless tube of 40 cm length and 0.5 mm inner diameter, and passage from the branching unit 5 to the confluence unit 6 was formed with a stainless tube of 5 cm length and 0.5 mm inner diameter, passage from the confluence unit 6 to the alcohol oxidase immobilized column 21 included in the detector unit 7 was formed with a polytetrafluoroethylene tube of 115 cm length and 0.5 mm inner diameter.

An pressure adjuster 30 to control a leak pressure resistance was formed with a polytetrafluoroethylene tube of 10 m length and 0.5 mm inner diameter so as to span from the branching unit 5 to the waste liquor bottle 10.

Each pump was of single plunger delivery type, of which delivery rate was set at: 0.8 ml/min. for the first pump 1, 1.0 ml/min. for the second pump 3, wherein actual leak rate was about 0.73 ml/min.

(3) Measurement Method and Results

Figure 8:
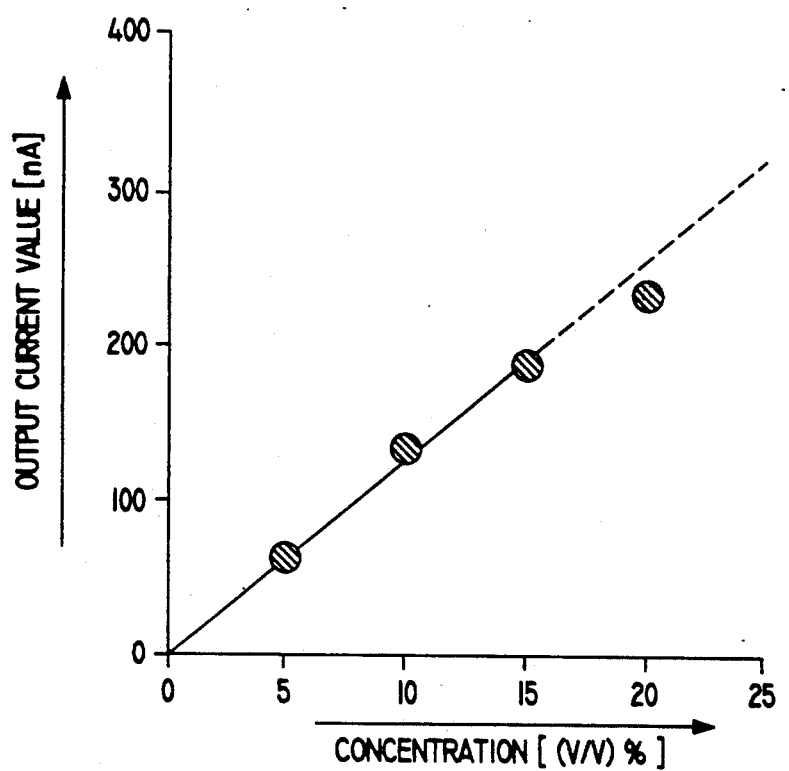
FIGS. 8 and 9 show graphs which were obtained by measurements conducted with use of the alcohol sensing device as shown in FIG. 4.

After a temperature equilibrium was obtained at the thermostat 20, 5 µl of ethyl alcohol aqueous solution each having 5.0, 10.0, 15.0, 20.0 (v/v) % was input into the flow line, for which run the output current values for each concentration were determined for 1 min. and the working line found was shown in FIG. 8.

Therein the output current value coefficient for a unit concentration was found to be 13.03 nA/(v/v) %. The working line indicates a linear relationship in the range of 5.0 to 15.0 (v/v) %, but at 20.0 (v/v) % concentration, the result is out of the linear relationship range.

COMPARATIVE EMBODIMENT 5

(1) the detector unit was the same as in the foregoing embodiment 5.

(2) Systems for Measurements

From the layout of the embodiment 5, the branching unit 5, the second pump 3, and the confluence unit 6 were removed. Hence the sample input unit 4 and the alcohol oxidase immobilized column 21 included in the detector unit 7 was connected with a polytetrafluoroethylene tube of 170 cm length and 0.5 mm inner diameter. And the first pump 1 was set to have 1.0 ml/min. rate.

(3) Measurement Method and Results

The output current values measured by this alcohol detector unit have a limited range for giving the linear relationship, because hydrogen peroxide produced by the immobilized enzyme column depends on an oxygen concentration dissolved in the solution. The upper limit of the linear range with current outputs was tried to be found with use of a thin alcohol range of 0.1 to 2.0 (v/v) %. The result was approximate 380 nA and also found was that measurements are not permitted without use of the dilution system of the present invention in a range above about 1.8%.

Therein the output current value coefficient for a unit concentration was found to be 199.4 nA/(v/v) %.

Evaluation of this comparative embodiment 5 against the foregoing embodiment 5 proved that the operation in the embodiment 5 diluted the input sample 15.3 times as compared to the comparative operation.

EMBODIMENT 6

(1) the detector unit was the same as in the foregoing embodiment 5.

(2) System for Measurements

Pulverized fiber brick particles (60 to 80 mesh sieved) were packed in a polytetrafluoroethylene tube of 20 cm length and outer, inner diameter; 3 mm, 2 mm. This packed tube was applied as a mixing tube and set to span between the sample injection unit 4 and the branching unit 5. Otherwise the same units or devices as in the embodiment 5 were used.

(3) Measurement Method and Results

Figure 9:
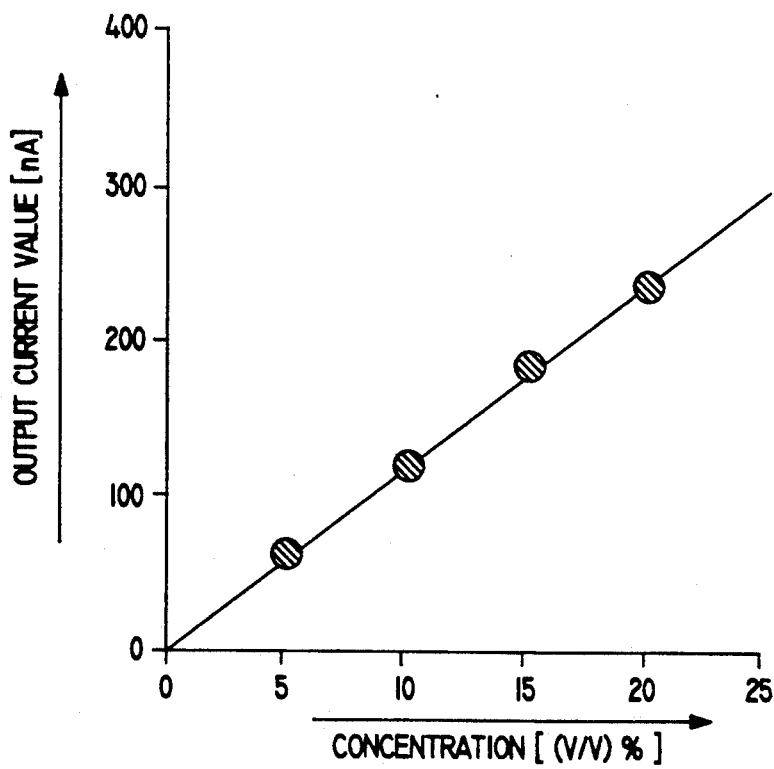

After a temperature equilibrium was obtained at the thermostat 20, 5 µl of ethyl alcohol aqueous solution each having 5.0, 10.0, 15.0, 20.0 (v/v) % was input into the flow line, for which run the output current values for each concentration were determined and the working line found was shown in FIG. 9.

In this case, measured data were found to agree accurately with the linear working line until 20.0 (v/v) %, which was a higher concentration obtained in the embodiment 5. This superiority is attributable to the improvement of mixing in this example as compared to the embodiment 5.

Therein the output current value coefficient for a unit concentration was found to be 11.83 nA/(v/v) %.

As has become apparent, the flow type dilution system of the present invention accomplishes the liquid mixtures with continuity and for short time, which merits contribute to continuous operation of samplings, dilutions, and detections with fastness and accuracy in flow injection measurements.

What is claimed is:

1. A liquid dilution system for analytical measurement comprising: a first carrier means for feeding a first carrier; a sample injection means for injecting a sample to be analyzed into the first carrier; a main passage for flowing a liquid from the sample injection means to an analytical measurement means; a branching means located downstream of the sample injection means for forming a branched passage to remove a liquid mass partially from the main passage; a confluence means located downstream of the branching means for confluencing a second carrier; and a second carrier means for feeding the second carrier to the confluence means.

2. A liquid dilution system as defined in claim 1, wherein a pressure resistance means is disposed in the branched passage.

3. A liquid dilution system as defined in claim 1, wherein a suction means for sucking partial liquid mass from the main passage is disposed in the branched passage.

4. A liquid dilution system as defined in claim 1, wherein the first carrier means and the second carrier means each comprise a delivery pump, and an inside volume of a branch chamber in the branching means is larger than one delivery volume made by one pumping action of either of the delivery pumps.

5. A liquid dilution system as defined in any one of claims 1-4, wherein a mixing tube for causing a turbulence in the main passage is disposed between locations of the sample injection means and the branching means.

6. A liquid dilution system as defined in claim 5, wherein the mixing tube comprises a pipe containing particles packed inside thereof.

* * * * *